(12) United States Patent
Vasudevan et al.

(10) Patent No.: US 8,501,484 B2
(45) Date of Patent: Aug. 6, 2013

(54) PREPARATION OF CERIUM HALIDE SOLVATE COMPLEXES

(75) Inventors: Kalyan V. Vasudevan, Los Almos, NM (US); Nickolaus A. Smith, Santa Fe, NM (US); John C. Gordon, Los Alamos, NM (US); Edward A. McKigney, Los Alamos, NM (US); Ross E. Muenchausen, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 13/420,159

(22) Filed: Mar. 14, 2012

(65) Prior Publication Data

US 2012/0238733 A1  Sep. 20, 2012

Related U.S. Application Data

(60) Provisional application No. 61/452,208, filed on Mar. 14, 2011, provisional application No. 61/500,043, filed on Jun. 22, 2011, provisional application No. 61/525,947, filed on Aug. 22, 2011.

(51) Int. Cl.
*G01N 33/20* (2006.01)

(52) U.S. Cl.
USPC .......................................................... 436/81

(58) Field of Classification Search
None
See application file for complete search history.

(56) References Cited

U.S. PATENT DOCUMENTS

| 5,827,602 A | 10/1998 | Koch et al. |
| 2010/0301219 A1 | 12/2010 | Boatner et al. |

FOREIGN PATENT DOCUMENTS

WO  WO 01/93363  12/2001

OTHER PUBLICATIONS

Izod et al, A Convenient Route to Lanthanide Triiodide THF Solvates. Crystal Structures of LnI3(THF)4 [Ln = Pr] and LnI3(THF)3.5 [Ln = Nd, Gd, Y], Inorg. Chem., 2004, 43, 214-218.*
Vasudevan et al., "An Ionic Liquid-Mediated Route to Cerium(III) Bromide Solvates," Inorganic Chemistry, 2011, vol. 50, pp. 4627-4631, published Apr. 8, 2011.
Vasudevan et al., "Ionic Liquid mediated routes to polydenate oxygen-donor adducts of cerium(III) bromide," Dalton Trans., 2012, vol. 41, pp. 1924-1927, published Dec. 23, 2011.
Shah et al., "CeBr$_3$ Scintillators for Gamma-Ray Spectroscopy," IEEE Transactions on Nuclear Science, vol. 52, No. 6, Dec. 2005, pp. 3157-3159.
Hagiwara et al., "Room Temperature Ionic Liquids of Alkylimidazolium Cations and Fluoroanions," J. Fluorine Chem., Sep. 2000, vol. 105, pp. 221-227.
Crostwaite et al., "Phase transition and decomposition temperatures, heat capacities and viscosities of pyridinium ionic liquids", J. Chem. Thermodynamics, Jun. 2005, vol. 37, pp. 559-568.
Sun et al., "Room-Temperature Molten Salts Based on the Quaternary Ammonium Ion," J. Phys. Chem. B, 1998, vol. 102, pp. 8858-8864.

(Continued)

*Primary Examiner* — Paul Dickinson
(74) *Attorney, Agent, or Firm* — Samuel L. Borkowsky

(57) ABSTRACT

Crystals of a solvated cerium(III) halide solvate complex resulted from a process of forming a paste of a cerium(III) halide in an ionic liquid, adding a solvent to the paste, removing any undissolved solid, and then cooling the liquid phase. Diffusing a solvent vapor into the liquid phase also resulted in crystals of a solvated cerium(III) halide complex.

10 Claims, 12 Drawing Sheets

(56) References Cited

OTHER PUBLICATIONS

Gaillard et al., "Competitive Complexation of Nitrates and Chlorides to Uranyl in a Room Temperature Ionic Liquid," Inorganic Chemistry, 2010, vol. 49, pp. 6484-6494, published online Jun. 17, 2010.

Nockemann et al., "Speciation of Rare-Earth Metal Complexes in Ionic Liquids: A Multiple-Technique Approach," Chem. Eur. J., 2009, vol. 15, No. 6, pp. 1449-1461, published online Jan. 2, 2009.

Mudring et al., "Ionic Liquids for Lanthanide and Actinide Chemistry," Euro. J. Inorg. Chem., Jun. 2010, vol. 18, pp. 2569-2581, published online May 27, 2010.

Binnemans et al., "Lanthanides and Actinides in Ionic Liquids," Chem. Rev. 2007, vol. 107(6), pp. 2592-2614, published on the web May 23, 2007.

Sheldrick, "A short history of SHELX," Acta Cryst. A, Jan. 2008, vol. 64, pp. 112-122.

Hitchcock et al., "Oxidation in Nonclassical Organolanthanide Chemistry: Synthesis, Characterization, and X-ray Crystal Structures of Cerium(III) and -(IV) Amides," Inorg. Chem., 2004, vol. 43, pp. 1031-1038, published online Dec. 31, 2003.

Natrajan et al., "Controlled Hydrolysis of Lanthanide Complexes of the N-Donor Tripod Tripod Tris(2-pyridylmethyl)amine versus Bisligand Complex Formation," Inorg. Chem., 2005, vol. 44, pp. 4756-4765.

Liddle et al., "Synthesis of Heteroleptic Cerium(III) Anionic Amido-Tethered N-Heterocyclic Carbene Complexes," Organometallics, 2005, vol. 24, pp. 2597-2605, published on web Apr. 19, 2005.

Barnhart et al., "Dissolution of Lanthanide and Actinide Metals Using Iodine and 2-Propanol. Synthesis and x-ray Crystal Structures of $Ln_3(HO\text{-}i\text{-}Pr)_4$ (Ln=La, Ce) and $Th_2I_4(O\text{-}i\text{-}Pr)_4(HO\text{-}i\text{-}Pr)_2$," Inorg. Chem., Sep. 1995, vol. 34, pp. 4862-4867.

\* cited by examiner

US 8,501,484 B2

PREPARATION OF CERIUM HALIDE SOLVATE COMPLEXES

RELATED APPLICATIONS

This application claims the benefit of U.S. Provisional Application 61/452,208 entitled "Preparation of Lanthanide Halide Solvate Complexes," filed Mar. 14, 2011, and U.S. Provisional Application 61/500,043 entitled "Preparation of Lanthanide Halide Complexes," filed Jun. 22, 2011, and U.S. Provisional Application 61/525,947 entitled "Preparation of Lanthanide Halide Solvate Complexes," filed Aug. 22, 2011, all incorporated by reference herein.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to the preparation of cerium(III) halide solvate complexes.

BACKGROUND OF THE INVENTION

The development of lanthanide coordination chemistry depends on the availability of suitable precursors. Many lanthanide halides are oligomers having low solubilities in most organic solvents. Their low solubility often limits their use as suitable precursors to other lanthanide containing molecules. Much attention has been devoted to the development of synthetic routes to lanthanide halide materials with better solubilities. These materials tend to be complexes of lanthanide halides with donor ligands that are coordinated (i.e. attached) to the lanthanide. Many of these complexes include oxygen- or nitrogen-containing donor ligands, where the oxygen or nitrogen is coordinated to the lanthanide.

Better routes for synthesizing lanthanide halide complexes are desirable.

SUMMARY OF THE INVENTION

In accordance with the purposes of the present invention, as embodied and broadly described herein, the present invention includes a process for preparing cerium halide solvate complexes. The process includes forming a paste of a cerium halide and a suitable ionic liquid and then dissolving at least a portion or all of the paste into a suitable organic solvent to form a liquid phase and a solid phase. The liquid phase is separated from any remaining solid phase. Afterward, crystals of the complex are formed from the liquid phase. The formation of the crystals may involve cooling the liquid phase, evaporation of solvent, or diffusion of another solvent into the liquid phase. The result is formation of crystals of the cerium halide solvate complex from the liquid phase.

The invention also relates to a process for preparing cerium halide solvate complexes that involves the addition of a suitable ionic liquid to a cerium halide solvate in the presence of a coordinating solvent different from the solvate molecule. This process facilitates the conversion of a cerium halide solvate complex to a different cerium halide solvate complex.

The invention also relates to complexes of the formula $CeX_3(solvent)_q$ or of the formula $[CeX_2(solvent)_n][CeX_4(solvent)_m]$, wherein X is selected from the group consisting of fluoride, chloride, bromide, and iodide, wherein q is 1, 2, 3, 4, or 5, wherein n is 1, 2, 3, 4, or 5, and wherein m is 1, 2, 3, 4, or 5, and wherein solvent is selected from the group consisting of an ether, a carboxylic acid, an ester, an aldehyde, 2-methyl-tetrahydrofuran, a thiol, a thioether, a thioester, a thioaldehyde, tetrahydrothiophene, a thiocarboxylic acid, a nitrile, pyridine, a polypyridine, and a phosphine, or a mixture of these solvents.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1:
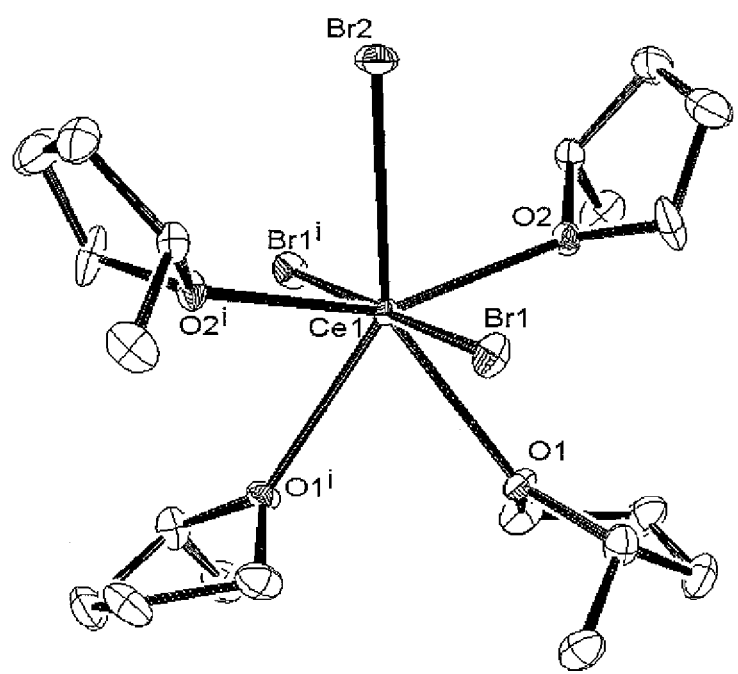
FIG. 1 shows an ORTEP of complex 3 (i.e. $CeBr_3(2\text{-Me-THF})_4$) with thermal ellipsoids shown at 40% probability. All hydrogen atoms have been omitted for clarity.

This invention relates to the preparation of lanthanide halide solvate complexes. In particular, this invention relates to the preparation of cerium halide solvate complexes, which include cerium(III) fluoride solvate complexes, cerium(III) chloride solvate complexes, cerium(III) bromide solvate complexes, and cerium(III) iodide solvate complexes. These complexes are expected to be scintillators, which are used in medical devices, screens, counters, probes, and for radiation detection applications. An embodiment composition of this invention has the formula $CeX_3(solvent)_q$ or of the formula

[CeX$_2$(solvent)$_n$][CeX$_4$(solvent)$_m$], wherein X is selected from the group consisting of fluoride, chloride, bromide, and iodide, wherein q is 1, 2, 3, 4, or 5, wherein n is 1, 2, 3, 4, or 5, wherein m is 1, 2, 3, 4, or 5, and wherein solvent is selected from the group consisting of an ether, a carboxylic acid, an ester, an aldehyde, 2-methyl-tetrahydrofuran, a thiol, a thioether, a thioester, a thioaldehyde, tetrahydrothiophene, a thiocarboxylic acid, a nitrile, pyridine, a polypyridine, and a phosphine, or a mixture of these solvents.

An aspect of this invention relates to the preparation of monomeric cerium halide solvate complexes. It is expected that at least some of these complexes are scintillators.

An embodiment preparation of cerium halide solvate complexes involves combining (by blending and/or milling, and the like) a suitable ionic liquid ("IL") with bulk cerium halide with subsequent centrifugation to isolate a paste. The resulting paste is at least partially or completely dissolved in an organic solvent and the undissolved solids (i.e. a solid phase) are separated by filtration or centrifugation. From the resulting liquid phase, which is the filtrate or supernatant, crystals of a monomeric cerium halide solvate complex are obtained by crystallization at room temperature, manipulation of temperature (i.e. cooling) or diffusion of another solvent into the filtrate.

Another embodiment preparation of cerium halide solvate complexes involves combining an ionic liquid with a first cerium halide solvate complex in the present of a coordinating solvent. The coordinating solvent is different from the solvate (i.e. the solvated ligand attached to the cerium) of the first cerium halide solvate. The presence of the ionic liquid facilitates the conversion of the first cerium halide solvate complex to the second cerium halide solvate complex.

Suitable halides for these cerium halides include fluorides, bromides, chlorides, and iodides.

Suitable ionic liquids for this invention are salts that have a melting temperature below 300° C.

Suitable ionic liquids for the preparation of cerium halide solvate complexes include 1-butyl-1-methylpyrrolidinium bis(trifluoromethylsulfonyl)imide and 1-butyl-3-methylimidazolium bis(trifluoromethylsulfonyl)imide. Other suitable ionic liquids include salts having the bis(trifluoromethylsulfonyl)imide anion combined with various imidazolium cations such as 3-ethyl-1,2-dimethyl imidazolium. A non-exhaustive list of suitable ionic liquids, at least some of which are molten salts at a temperature at or below 100° C. is provided by Hagiwara et al. in "Room Temperature Ionic Liquids of Alkylimidazolium Cations and Fluoroanions", *J. Fluorine Chem.* vol. 105, (2000), pp. 221-227, incorporated by reference herein. PCT Patent Application WO 01/93363 to McEwen et al. entitled "Non-Flammable Electrolytes", also incorporated by reference, also provides a variety of suitable ionic liquids having a melting temperature at or below 100° C. that are expected to be useful ionic liquids with this invention. A non-exhaustive list of some suitable ionic liquids with melting points between 100° C.-300° C. are provided in "Phase transition and decomposition temperatures, heat capacities and viscosities of pyridinium ionic liquids", *J. Chem. Thermodynamics* vol. 37, (2005), pp. 559-568, incorporated by reference. Some organic cations of molten salts (i.e. ionic liquids) that are useful with, or expected to be useful with, this invention include alkyl-substituted organic cations of pyridinium, pyrrolidinium, pyridazinium, pyrimidinium, pyrazinium, imidazolium, pyrazolium, thiazolium, oxazolium, and triazolium. "Room-Temperature Molten Salts Based on the Quaternary Ammonium Ion," *J. Phys. Chem. B*, 1998, vol. 102, pages 8858-8864, incorporated by reference herein, and U.S. Pat. No. 5,827,602 to Koch et al. entitled "Hydrophobic Ionic Liquids," which issued Oct. 27, 1998 and also incorporated by reference herein, provide other examples of ionic liquids that are expected to be suitable ionic liquids for use with this invention.

Suitable solvents are liquids that can dissolve at least some of the paste and form solvate complexes with the cerium halide. These include, but are not limited to, ethers (e.g. diethylether, di-isopropylether, diphenylether), carboxylic acids (e.g. formic acid, acetic acid, stearic acid), esters (e.g. butyl butyrates, benzyl acetate, ethyl formate), aldehydes (e.g. benzaldehyde, butyraldehyde, acetaldehyde), 2-methyl-tetrahydrofuran, thiols (e.g. methanethiol, butanethiol, tert-butyl mercaptan, thioethers (e.g. dimethylsulfide, diethylsulfide, thioanisole), thioesters (e.g. S-methyl thioacetate, S-tertbutyl thioacetate, S-ethyl thiopropionate), tetrahydrothiophene, thiocarboxylic acids (e.g. 2,6-pyridinedicarbothioic acid), nitriles (e.g. acetronitrile, benzonitrile, glutaronitrile), pyridines (e.g. 2-methylpyridine, 3,5-dimethylpyridine, 4-methylpyridine), amines (e.g. tert-butylamine, isopropylamine, aniline) and phosphines (e.g. triethylphosphine, trimethylphosphine).

In an embodiment, crystals of the solvate complex CeBr$_3$(2-Me-THF)$_4$ were prepared using cerium(III) bromide as the lanthanide halide, 1-butyl-1-methylpyrrolidinium bis(trifluoromethylsulfonyl)imide as the ionic liquid, and 2-methyl-tetrahydrofuran ("2-Me-THF") as the organic solvent.

The EXAMPLES below are provided to illustrate some non-limiting embodiments of this invention and demonstrate the operability of the invention. All manipulations in these EXAMPLES were carried out under an argon atmosphere by using standard SCHLENK techniques or inside a VACUUM ATMOSPHERES glove box. Anhydrous solvents were purchased from either SIGMA ALDRICH or ACROS and stored over molecular sieves. CeBr$_3$ and LaBr$_3$ were purchased from SIGMA ALDRICH as 99.999% pure materials and were used without further purification. The ionic liquid 1-butyl-1-methylpyrrolidinium bis(trifluoromethylsulfonyl)imide was prepared according to a literature procedure (see: Gaillard et al., *Inorganic Chemistry*, 2010, vol. 49, pp. 6484; Nockemann et al., *Chem. Eur. J.*, 2009, 15(6), pp. 1449-1461; Mudring et al., *Euro. J. Inorg. Chem.*, 2010, vol. 18, pp. 2569-2581; Binnemans et al., 2007, vol. 107(6), pp. 2592-2614, all incorporated by reference herein). All reagents were purchased from SIGMA ALDRICH and used without further purification. Elemental Analysis was performed by MIDWEST MICROLAB, LLC and ATLANTIC MICROLAB, LLC. Nuclear Magnetic Resonance ("NMR") spectra were recorded at ambient temperature on a BRUKER AV-400 spectrometer. X-ray diffraction data were collected by mounting crystals under PARATONE on glass fiber loops on a BRUKER APEX II system fitted with an OXFORD nitrogen cryostream. Structure solution and refinement against F$^2$ were performed using SHELX97 (see: Sheldrick, Acta Cryst. A, 2008, vol. 64, pp. 112-122, incorporated by reference herein). FTIR data were collected using a BRUKER VERTEX 80V FT-IR spectrometer equipped with an MVP-pro Attenuated Total Reflection (ATR) attachment with a diamond window at 4 cm$^{-1}$ resolution.

Example 1

Preparation of a paste of CeBr$_3$/1-butyl-1-methylpyrrolidinium bis(trifluoromethylsulfonyl)imide (1): CeBr$_3$ (104.2 grams, 0.274 moles) and 1-butyl-1-methylpyrrolidinium bis(trifluoromethylsulfonyl)imide (380 milliliters) were mixed together and homogenized in a commercial blender. The mixture was introduced into a NETZSCH MINICER bead mill fitted with a peristaltic pump to allow for continuous flow. A HUBER NUEVO UNISTAT 425 chiller was used during the milling procedure to control the temperature, which was below 20° C. The mill speed was 1500 rpm, and milling time was approximately 8 hours. The product was centrifuged with a SORVALL WX ULTRA 80 centrifuge at 40,000 rpm for approximately 3 hours. After decanting the supernatant, the resulting paste (1) was approximately 40% v/v $CeBr_3$ and 1-butyl-1-methylpyrrolidinium bis(trifluoromethylsulfonyl) imide.

Example 2

Preparation of $CeBr_3(THF)_4$ 2: tetrahydrofuran ("THF") (5 milliliters) was added to 2.50 grams of the paste of prepared from EXAMPLE 1. The mixture was stirred for approximately 5 minutes. The undissolved solids were allowed to settle, and the mixture was then filtered. The clear, colorless filtrate was stored at a temperature of $-35°$ C. for 2 days, affording a crop of colorless crystalline plate-shaped crystals. The crystals were washed with cold THF (5 ml) and dried under argon. The identity of the crystals was confirmed by matching the single-crystal X-ray diffraction unit cell to the published structure [see: Hitchcock et al., *Inorg. Chem.*, 2004, vol. 43, pp. 1031-1038). Yield: 0.456 grams. The FT-IR spectrum included a peak at 1018 cm-1 assigned to a C—O stretch (the C—O stretch of neat THF occurs at 1070 cm-1). Analysis calculated for $C_{16}H_{32}O_4CeBr_3$: C (28.76%), H (4.83%). Found: C (28.45%), H (4.72%).

Example 3

Preparation of $CeBr_3$(2-Me-THF)$_4$ (complex 3): 5 milliliters of 2-methyl-tetrahydrofuran ("2-Me-THF") was added to 1.00 grams of the paste prepared from EXAMPLE 1. The mixture was stirred for approximately 5 minutes. The undissolved solids were allowed to settle and the supernatant was decanted away from the undissolved solids. Hexanes (1 ml) were added to the supernatant. The resulting solution was filtered. The filtrate was stored at a temperature of $-35°$ C. for one week, affording colorless crystalline blocks of crystals of 3. The crystals of 3 were washed with cold 2-Me-THF and dried under argon. Yield (0.115 grams). The FT-IR spectrum included a peak at 1057 cm$^{-1}$ assigned to a C—O stretch (the C—O stretch for neat 2-Me-THF is at 1065 cm—1). Analysis calculated for $C_{20}H_{40}O_4CeBr_3$: C (33.16%), H (5.57%). Found: C (20.71%), H (3.44%) corresponding to $CeBr_3$(2-Me-THF)$_{1.9}$. An ORTEP representation of 3 is shown in FIG. 1. All hydrogen atoms have been omitted for clarity.

Example 4

Figure 2:
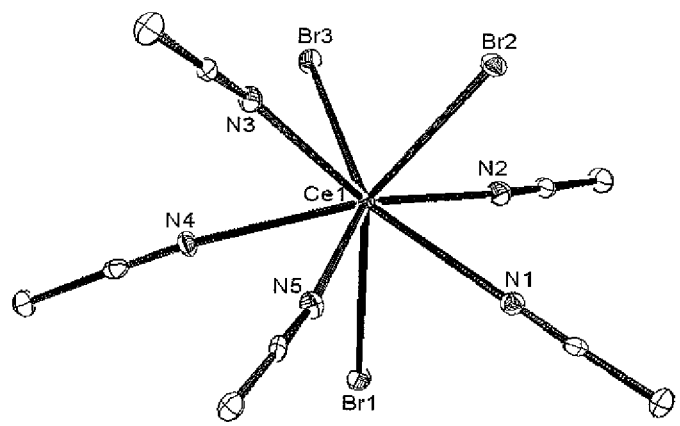
FIG. 2 shows an ORTEP view of complex 4 (i.e. $CeBr_3(CH_3CN)_5 \cdot (CH_3CN)$) with thermal ellipsoids shown at 40% probability. All hydrogen atoms and lattice MeCN (i.e. $CH_3CN$) have been omitted for clarity.

Preparation of $CeBr_3(CH_3CN)_5.(CH_3CN)$ (complex 4): five milliliters of acetonitrile ($CH_3CN$) were added to 2.50 grams of the paste prepared from EXAMPLE 1. The mixture was stirred for approximately 5 minutes. The undissolved solids were allowed to settle and the supernatant was decanted away from the undissolved solids and then the clear colorless supernatant was stored at a temperature of $-35°$ C. for 2 days, affording a crop of colorless plate-shaped crystals. The crystals were washed twice with cold acetonitrile (2×1 ml) and dried under argon. Yield: 0.420 grams. After 30 minutes at ambient temperature, the crystals had changed to a white powder. The FT-IR spectrum included a peak at 2273 cm$^{-1}$ assigned to a CN stretch (the CN stretch for neat acetonitrile appears at 2254 cm$^{-1}$). Analysis calculated for $C_{13}H_{18}N_6CeBr_3$: C (23.02%), H (2.88%). Found: C (13.55%), H (1.79%), corresponding to $CeBr_3(CH_3CN)_{2.8}$. An ORTEP representation of 4 is shown in FIG. 2. All hydrogen atoms have been omitted for clarity.

Example 5

Figure 3:
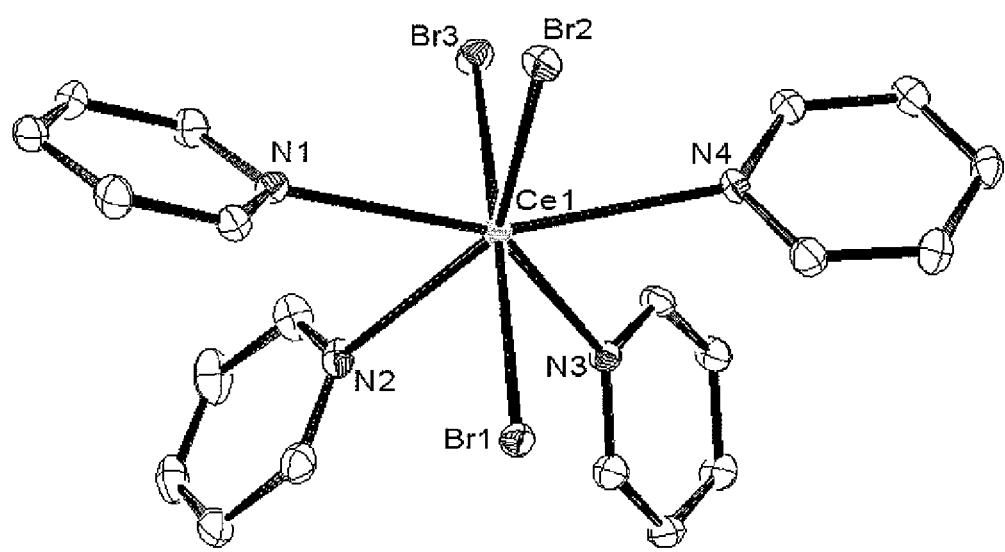
FIG. 3 shows an ORTEP view of complex 5 (i.e. $CeBr_3(pyridine)_4$) with thermal ellipsoids shown at 40% probability. All hydrogen atoms have been omitted for clarity.

Preparation of $CeBr_3$(pyridine)$_4$ (complex 5): Pyridine (1 milliliter) was added to $CeBr_3(THF)_4$ (2) (0.10 grams, 0.15 millimoles) and the resulting solution was stirred for approximately 1 minute. Toluene was added dropwise until the solution became cloudy. The resulting mixture was filtered. The filtrate was collected and stored at room temperature for 2 days, affording a crop of large colorless needle-shaped crystals. The crystals were separated by filtration, washed with cold toluene, and dried in vacuo. Toluene was added to the mother liquor and the crystallization process was repeated twice more. The combined crops of crystals were washed once more with cold toluene (1 ml) and dried in vacuo. Yield: (0.045 grams, 51%). The FT-IR spectrum included peaks at 1599 and 1442 cm$^{-1}$ (by comparison, C═C and C═N stretches in neat pyridine appear, respectively, at 1582 and 1439 cm$^{-1}$). An ORTEP representation of 5 is shown in FIG. 3. All hydrogen atoms have been omitted for clarity.

Example 6

Figure 4:
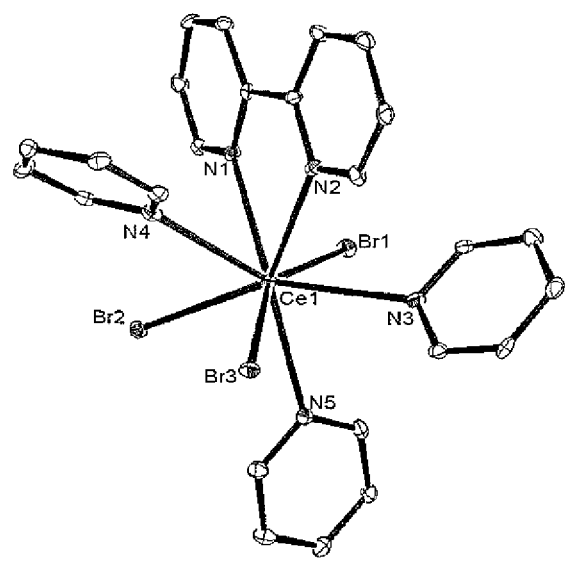
FIG. 4 shows an ORTEP view of complex 6 (i.e. $CeBr_3(bipyridine)(pyridine)_3$) with thermal ellipsoids shown at 40% probability. All hydrogen atoms have been omitted for clarity.

Preparation of $CeBr_3$(bipyridine)(pyridine)$_3$ (complex 6): A suspension of $CeBr_3(THF)_4$ (complex 2) (0.050 grams, 0.075 millimoles) in dichloromethane (10 milliliters) was prepared. A solution of bipyridine (0.023 grams, 0.150 millimoles) in dichloromethane was prepared and added to the suspension. After allowing the resulting yellow suspension to continue stirring overnight, the reaction mixture was allowed to settle. The solvent was decanted. The yellow solid was washed twice with cold dichloromethane to remove unreacted bipyridine. The solid was dried in vacuo, affording a bright yellow solid. A saturated solution of the yellow solid in pyridine was prepared. Slow diffusion of hexanes into the saturated solution produced yellow block-shaped crystals of $CeBr_3$(bipyridine)(pyridine)$_3$ (complex 6) that proved to be suitable for X-ray diffraction. The crystals were washed with cold toluene and dried under argon. Yield: 0.035 grams, 62%). The FT-IR spectrum included peaks at 1600 and 1441 cm$^{-1}$ assigned to pyridine C═C and C═N stretches (compared to 1541 and 1439 cm$^{-1}$, respectively, for neat pyridine), and peaks at 1595 and 1436 cm$^{-1}$ assigned to C═C and C═N stretches for bipyridine. Analysis calculated for $C_{25}H_{23}N_3CeBr_3$: C (38.83%), H (3.00%), N (9.06%). Found: C (37.71%), H (2.81%), N (8.58%). An ORTEP representation of 6 is shown in FIG. 4. Hydrogen atoms were omitted for clarity.

Example 7

Preparation of $LaBr_3(THF)_4$ (complex 7): Lanthanum bromide ($LaBr_3$, 0.50 grams, 1.32 millimoles) was added to THF (10 milliliters) and the mixture was stirred at 55° C. for 30 minutes. Undissolved solid was allowed to settle out, and the mixture was filtered. The filtrate was stored at room temperature for 2 hours, affording a crop of colorless block-shaped crystals of $LaBr_3(THF)_4$ (complex 7). The crystals were isolated and dried under argon. Yield: 0.065 grams). A FT-IR spectrum of the product included a peak at 1018 cm$^{-1}$ assigned to a C—O stretch (by comparison, the C—O stretching peak for neat THF appears at 1070 cm$^{-1}$). Analysis calculated for $C_{16}H_{32}O_4LaBr_3$: C (28.82%), H (4.84%). Found: C (28.26%), H (4.75%).

Example 8

Figure 5:
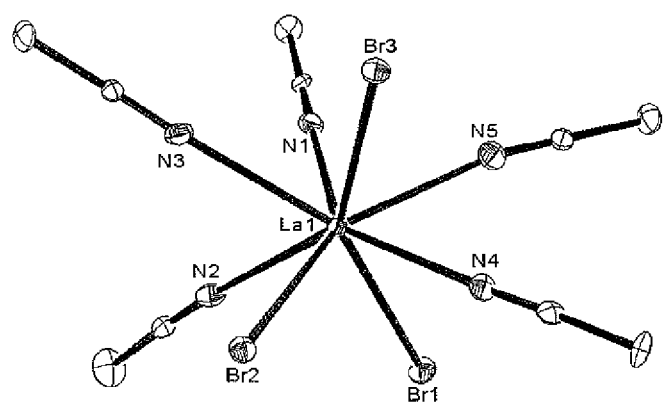
FIG. 5 shows an ORTEP view of complex 8 (i.e. $LaBr_3(MeCN)_5 \cdot 2MeCN$) with thermal ellipsoids shown at 40% probability. All hydrogens have been omitted for clarity.

Preparation of LaBr$_3$(MeCN)$_5$·2MeCN (complex 8): LaBr$_3$ (0.50 g, 1.32 millimoles) was added to MeCN (10 milliliters) and the mixture stirred at 65° C. for 20 min. The undissolved solid was permitted to settle out and the solution was filtered. After cooling to room temperature, the resulting solution was stored at −35° C. overnight resulting in a crop of colorless, crystalline plates. The crystals were isolated and dried under argon. Yield (0.100 g). (FTIR; C≡N stretch of neat MeCN: 2254 cm$^{-1}$; (complex 8): 2273 cm$^{-1}$). Analysis calculated for C$_{14}$H$_{21}$N$_7$LaBr$_3$: C, 25.26 H, 3.15. Found: C, 19.61 H, 2.55; [CeBr$_3$(MeCN)$_{4.7}$)]. An ORTEP representation of 8 is shown in FIG. 5. Hydrogen atoms were omitted for clarity.

Example 9

Figure 6:
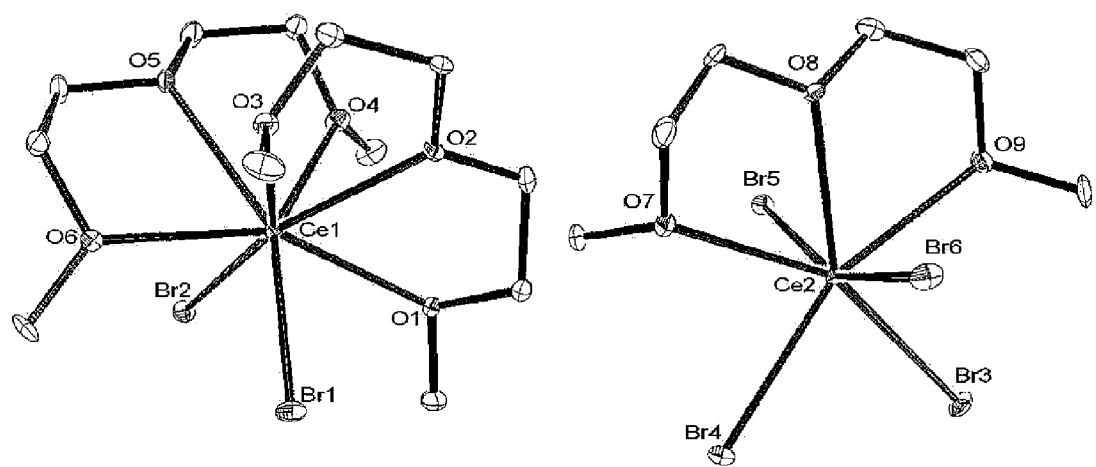
FIG. 6 shows an ORTEP view of complex 9 (i.e. $[CeBr_2(diglyme)_2][CeBr_4(diglyme)]$) with thermal ellipsoids shown at 40% probability. All hydrogen atoms have been omitted for clarity.

Preparation of [CeBr$_2$(diglyme)$_2$][CeBr$_4$(diglyme)] (complex 9): CeBr$_3$ (0.10 g, 0.263 millimoles) was suspended in THF (7 mL) and stirred at 55° C. for 15 minutes. The solution was cooled to room temperature and the solvent removed in vacuo. To the resulting solid was added the ionic liquid [BMP][Ntf$_2$] (0.05 g) and diglyme (7 mL). The resulting suspension was stirred at 140° C. for 20 minutes, during which time the solids dissolved and the resulting solution became transparent. The solution was filtered hot, cooled to room temperature and stored for 3 days, during which time a crop of crystalline blocks emerged. The solution was decanted and the resulting crystals washed with diglyme (2×2 mL) and toluene (2×2 mL). The crystals were dried in vacuo and isolated. Yield of complex 9 after drying: 0.110 g, 72%. An ORTEP representation of 9 is shown in FIG. 6. Hydrogen atoms were omitted for clarity. Anal. calcd for C$_{18}$H$_{42}$O$_9$Ce$_2$Br$_6$: C, 18.61 H, 3.62. Found: C, 18.91 H, 3.74; FTIR (Ce—Br, bold is most intense): 162 cm$^{-1}$, 146 cm$^{-1}$, 124 cm$^{-1}$.

Example 10

Figure 8:
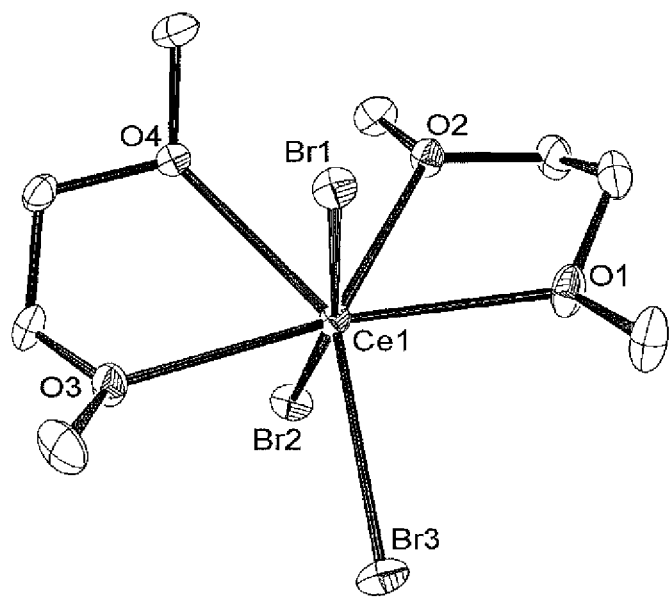
FIG. 8 shows an ORTEP view of complex 10 (i.e. $CeBr_3(dimethoxyethane)_2$) with thermal ellipsoids shown at 40% probability. All hydrogen atoms have been omitted for clarity.

Preparation of [CeBr$_3$(dimethoxyethane)$_2$] (complex 10): CeBr$_3$ (0.300 g, 0.790 mmol) was suspended in THF (5 mL) and stirred at 50° C. for 10 minutes. The solvent was removed in vacuo and dimethoxyethane (7 mL, dme) and 10 drops [BMP][NTf$_2$] were added to the white powder. The resulting suspension was stirred at 70° C. for 10 minutes, during which time the solution went transparent. The mixture was filtered hot and the resulting clear, colorless solution was cooled and the volume reduced by evaporation overnight resulting in a crop of colorless crystals. The mother liquor was decanted and the resulting crystals of complex 10 were washed sequentially with dimethoxyethane (5 mL) and Et$_2$O (10 mL) and dried in vacuo. (0.321 g, 72% yield). Analysis calculated for C$_8$H$_{20}$O$_4$CeBr$_3$: C, 17.16 H, 3.60. Found: C, 16.92 H, 3.39. FTIR (Ce—Br, bold is most intense): 175 cm$^{-1}$, 142 cm$^{-1}$. An ORTEP representation for 10 is shown in FIG. 8. Hydrogen atoms were omitted for clarity.

Example 11

Figure 9:
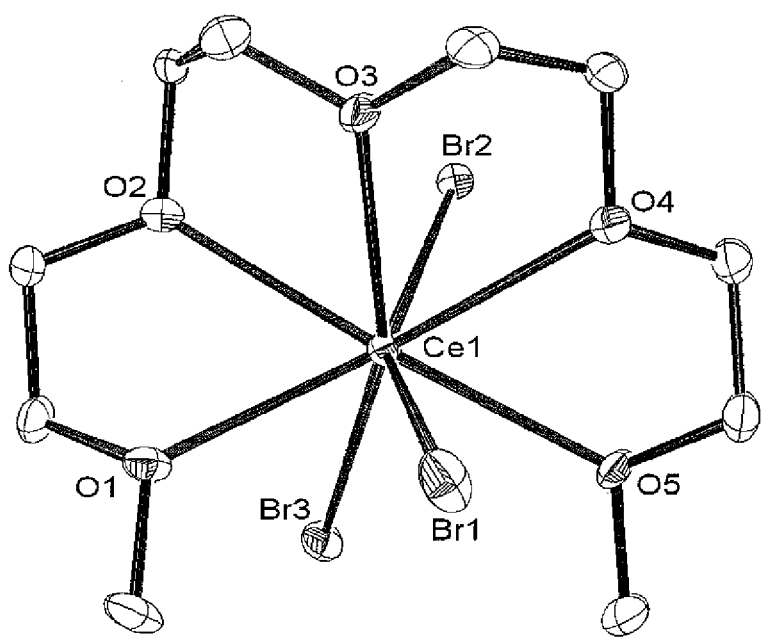
FIG. 9 shows an ORTEP view of complex 11 (i.e. $CeBr_3(tetraglyme)$) with thermal ellipsoids shown at 40% probability. All hydrogen atoms have been omitted for clarity.

Preparation of [CeBr$_3$(tetraglyme)] (complex 11): CeBr$_3$ (1.00 g, 2.63 mmol) was suspended in THF (5 mL) and stirred at 50° C. for 10 minutes. The solvent was removed in vacuo and tetraglyme (7 mL) and 75 drops [BMP][NTf$_2$] were added to the white powder. The resulting suspension was stirred at 180° C. for 10 minutes, during which time the solution went transparent and faintly yellow. The mixture was filtered hot and the resulting clear solution was cooled to room temperature slowly over the course of 24 hours resulting in a crop of colorless needles. The mother liquor was decanted and the resulting crystals of complex 11 were washed sequentially with tetraglyme (5 mL) and Et$_2$O (10 mL) and dried in vacuo. (1.110 g, 70% yield). Analysis calculated for C$_{10}$H$_{22}$O$_5$CeBr$_3$: C, 20.00 H, 3.61. Found: C, 20.17 H, 3.69. FTIR (Ce—Br, bold is most intense): 167 cm$^{-1}$, 129 cm$^{-1}$. An ORTEP representation for 11 is shown in FIG. 9. Hydrogens were omitted for clarity.

Figure 7A:
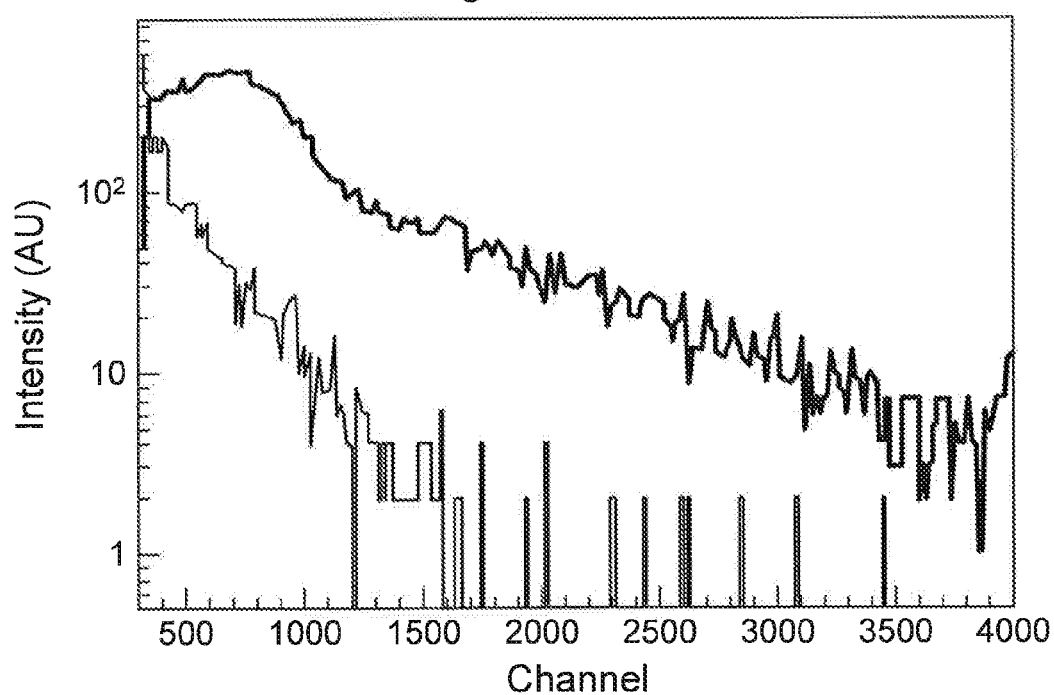
FIGS. 7a, 7b, and 7c show energy spectra of complex 9. The upper traces are the energy spectra using Co-57 (122 KeV (broad), Ba-133 (356 KeV, broad), and Cs-136 (662 KeV, narrow), respectively, and the lower traces are the backgrounds for reference these spectra were obtained using small crystals of the complex and show that a qualitative energy response for the complex, which suggests that complex 9 may be used as a scintillator.
Figure 7B:
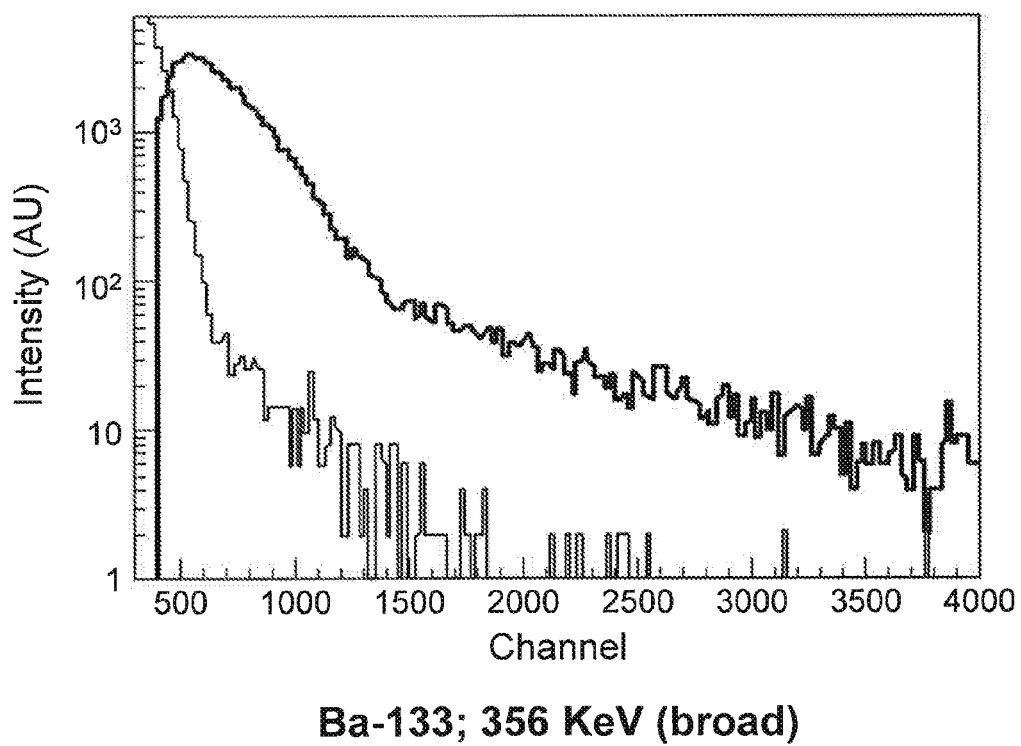
Figure 7C:
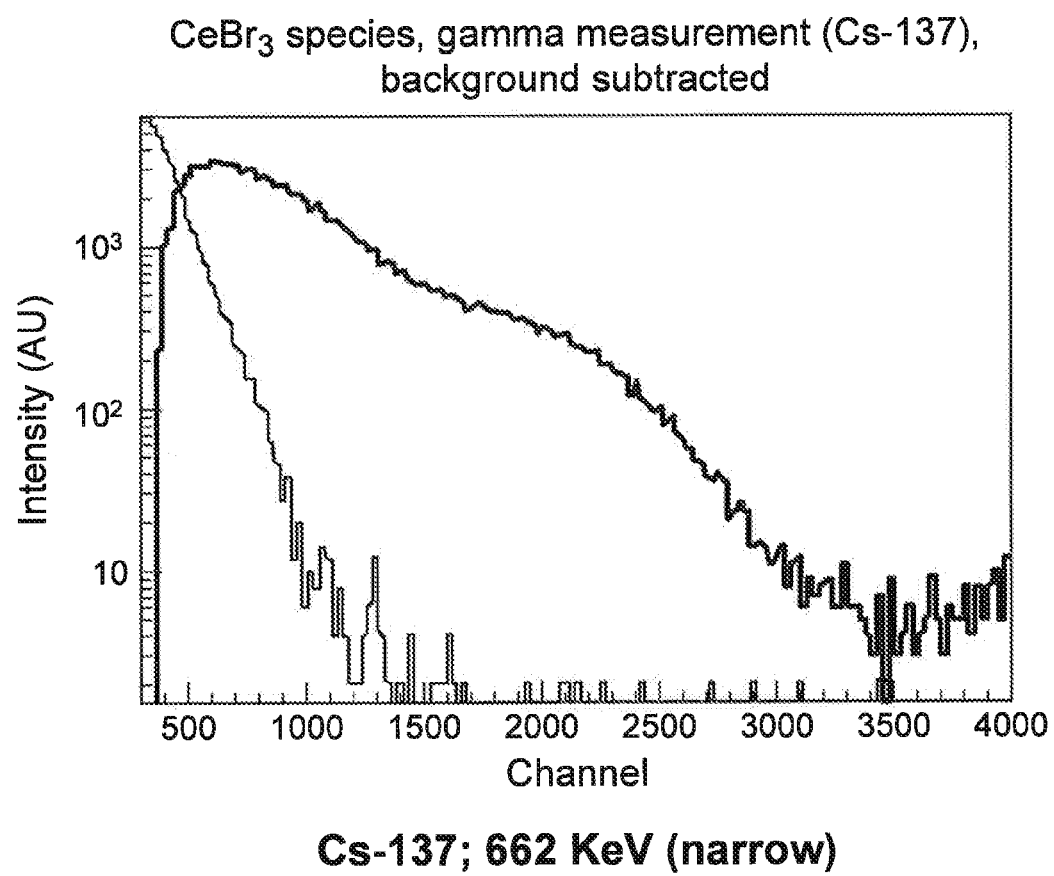
Figures 10A, 10B:
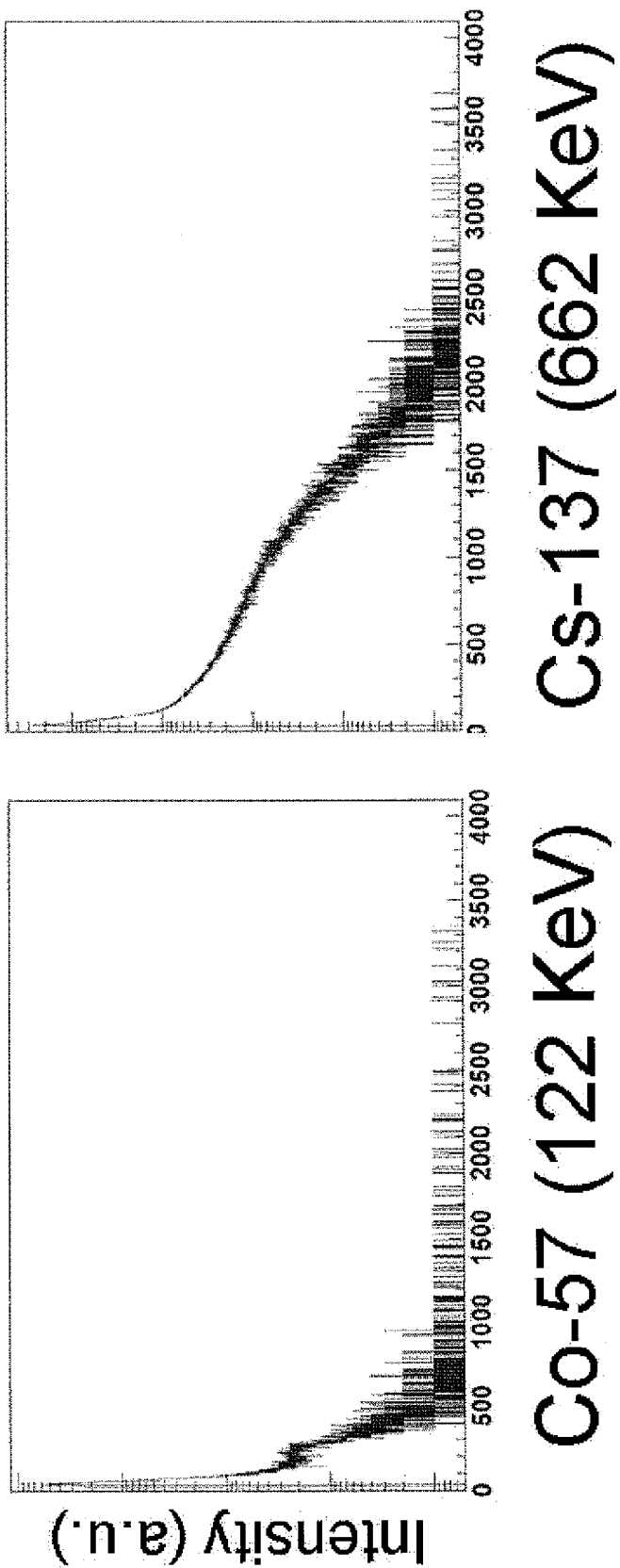
FIGS. 10a and 10b show energy spectra of complex 10 (i.e. $CeBr_3(dimethoxyethane)_2$) using Co-57 (122 KeV) (FIG. 10a) and Cs-137 (662 KeV) (FIG. 10b).

Energy spectra were obtained for the crystals of complex 9. Measurements using three different gamma-ray sources were performed. For each experiment, the crystals were placed in a reduced-volume cuvette (long-axis is 1 cm), and the cuvette was coupled to the front face of a photomultiplier tube with optical grease. The cuvette was placed such that the crystals were lined up parallel with the front face of the PMT. With this experiment set up, Co-57, Ba-133, and Cs-137 were used to test the gamma response of the crystals. If the crystals exhibited a response to the gamma-rays, then any features detected by the crystals-PMT detection system would shift according to the energy of the gamma-rays emitted by the sources. FIGS. 7a, 7b, and 7c show crystal response, i.e. the intensity in arbitrary units as a function of the gamma-ray energy. Co-57 (FIG. 7a) emitted an array of gamma-rays; the greatest intensity being 136 keV. Ba-133 (FIG. 7b) also exhibited multiple lines with 356 keV being the most intense. Cs-137 (FIG. 7c) emitted gamma-rays with energy of 662 keV. Energy spectra were also obtained for the crystals of complex 10. Measurements using two different gamma-ray sources were performed. Using the same setup noted for measurements of complex 9, Co-57 (FIG. 10a) and Cs-137 were use to test the gamma response of the crystals. FIGS. 10a and 10b show crystal response as a function of gamma-ray energy.

The precursor cerium halide/ionic liquid paste prepared according to EXAMPLE 1 was used without further purification for the synthesis of CeBr$_3$(THF)$_4$ (complex 2), CeBr$_3$ (2-Me-THF)$_4$ (complex 3) and CeBr$_3$(MeCN)$_5$·MeCN (complex 4). A summary of the overall synthetic scheme is presented in Scheme 1.

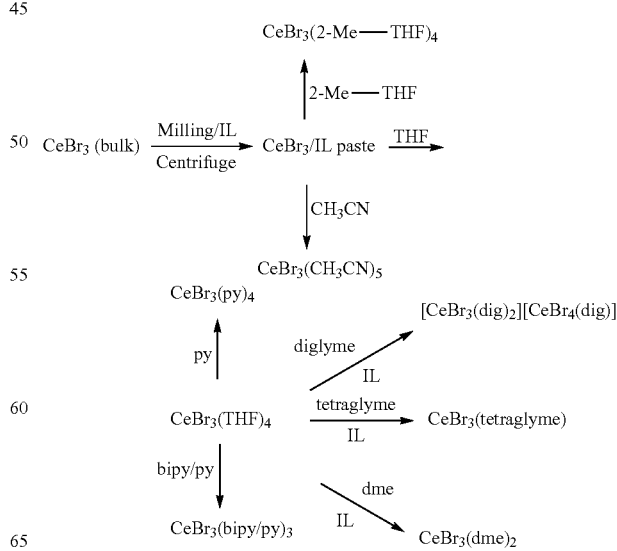

Scheme 1. Synthetic route to cerium(III) bromide solvate complexes.

Large crops of colorless, crystalline cerium halide solvate complexes 2-4 suitable for X-ray diffraction experiments were obtained from saturated solutions of 1 in their respective solvents at reduced temperature. The structure of complex 2 was confirmed by matching of the unit cell to the published structure of $CeBr_3(THF)_4$. The full data sets collected for cerium halide solvate complexes 3 and 4 resulted in the 2-Me-THF and MeCN adducts of $CeBr_3$ depicted in FIGS. 1 and 2, respectively.

The X-ray structures of cerium halide solvate complexes 3 and 4 reveal the presence of four bound 2-Me-THF and five bound acetonitrile ligands, respectively. The higher coordination number observed for complex 4 can be explained by the diminished steric demands of the acetonitrile ligand relative to the bulkier tetrahydrofuran analogs of solvate complexes 2 and 3. Addition of acetonitrile to complex 2 resulted in displacement of the THF solvating ligands, yielding a second synthetic pathway to complex 4.

The observation that the solvating THF ligands in complex 2 are readily displaced by acetonitrile led to the assertion that complex 2 may serve as a suitable precursor for the synthesis of other $CeBr_3$ adducts. Indeed, the reaction of complex 2 with pyridine results in, after work up, pure $CeBr_3(py)_4$ (solvate complex 5) (see FIG. 3).

A second pyridyl adduct was obtained from the reaction of bipyridine and complex 2 in dichloromethane solution. Subsequent recrystallization from pyridine and hexanes led to the formation of $CeBr_3(bipy)(py)_3$ (cerium halide solvate complex 6) as a yellow crystalline solid in good yield (see FIG. 4). Despite the presence of excess bipyridine in the reaction mixture, the crystal structure reveals the presence of a single bipyridine ligand bound to a $CeBr_3$ unit with the remaining coordination sphere being occupied by three pyridine ligands. Further emphasizing the synthetic utility of complex 2 is the observation that under identical reaction conditions, substitution of complex 2 with bulk $CeBr_3$ produces no apparent reaction.

Table 1 below summarizes X-ray crystal data for $CeBr_3$(2-Me-THF)$_4$ (complex 3), $CeBr_3(MeCN)_5 \cdot MeCN$ (complex 4), $CeBr_3(py)_4$ (complex 5), and Table 2 summarizes X-ray crystal data for $CeBr_3(bipy)(py)_3$ (complex 6) and $LaBr_3(MeCN)_5 \cdot 2MeCN$ (complex 8).

TABLE 1

| Complex | 3 | 4 | 5 |
|---|---|---|---|
| Empirical formula | $C_{20}H_{40}Br_3CeO_4$ | $C_{12}H_{18}N_6CeBr_3$ | $C_{20}H_{20}N_4C$ |
| M | 724.37 | 626.17 | 696.25 |
| T/K | 140(1) | 140(1) | 140(1) |
| Color | Colorless | Colorless | Colorless |
| Crystal system | Monoclinic | Monoclinic | Orthorhombic |
| Space group | C2/c | P2$_1$/n | Pbca |
| a/Å | 22.421(9) | 8.800(2) | 17.1142(11) |
| b/Å | 9.395(4) | 13.250(3) | 17.2768(11) |
| c/Å | 16.657(11) | 18.628(5) | 32.582(2) |
| β/° | 131.149(3) | 95.130(2) | 90.0 |
| u/Å$^3$ | 2641.4(9) | 2163.1(9) | 9633.7(11) |
| Z | 4 | 4 | 16 |
| Dc/Mg m$^{-3}$ | 1.821 | 1.923 | 1.920 |
| μ/mm$^{-1}$ | 6.281 | 7.65 | 6.879 |
| Crystal size/mm | 0.28 × 0.26 × 0.12 | 0.35 × 0.24 × 0.24 | 0.20 × 0.18 × 0.12 |
| Reflections collected | 13442 | 23229 | 90530 |
| R(int) | 0.0535 | 0.0363 | 0.0628 |
| Data/restraints/parameters | 3106/13/140 | 5136/0/205 | 8954/0/505 |
| Absorption correction | Semi-empirical | Semi-empirical | Semi-empirical |
| R1 [I > 2 (I)] | 0.0359 | 0.0276 | 0.0330 |
| wR2 (all data) | 0.1411 | 0.1053 | 0.0762 |
| Largest peak, hole/e Å$^{-3}$ | 0.996, −1.202 | 1.066, −0.989 | 0.618, −0.657 |

TABLE 2

| Complex | 6 | 8 |
|---|---|---|
| Empirical formula | $C_{25}H_{23}N_5CeBr_3$ | $C_{14}H_{21}N_7LaBr_3$ |
| M | 773.33 | 666.02 |
| T/K | 140(1) | 140(1) |
| Color | Yellow | Colorless |
| Crystal system | Monoclinic | Orthorhombic |
| Space group | Cc | P2$_1$2$_1$2$_1$ |
| a/Å | 16.770(4) | 8.995(2) |
| b/Å | 9.657(2) | 12.433(3) |
| c/Å | 17.881(4) | 21.698(5) |
| β/° | 115.304(2) | 90.0 |
| u/Å$^3$ | 2618.0(10) | 2426.8(10) |
| Z | 4 | 4 |
| Dc/Mg m$^{-3}$ | 1.962 | 1.823 |
| μ/mm$^{-1}$ | 6.341 | 6.710 |
| Crystal size/mm | 0.20 × 0.18 × 0.18 | 0.16 × 0.14 × 0.04 |
| Reflections collected | 11606 | 23106 |
| R(int) | 0.0297 | 0.0812 |
| Data/restraints/parameters | 4761/2/307 | 4411/0/233 |
| Absorption correction | Semi-empirical | Semi-empirical |
| R1 [I > 2 (I)] | 0.0257 | 0.0510 |
| wR2 (all data) | 0.0567 | 0.1216 |
| Largest peak, hole/e Å$^{-3}$ | 0.625, −0.594 | 1.396, −1.893 |

Table 3 below summarizes X-ray crystal data for [CeBr$_2$(diglyme)$_2$][CeBr$_4$(diglyme)] (complex 9), CeBr$_3$(dme)$_2$ (complex 10) and CeBr$_3$(tetraglyme) (complex 11)).

TABLE 3

|  | 9 | 10 | 11 |
|---|---|---|---|
| Empirical formula | C$_{18}$H$_{42}$Br$_6$Ce$_2$O$_9$ | C$_8$H$_{20}$O$_4$CeBr$_3$ | C$_{10}$H$_{22}$O$_5$CeBr$_3$ |
| M | 1162.22 | 560.09 | 602.10 |
| T/K | 140(1) | 140(1) | 140(1) |
| Color | Colorless | Colorless | Colorless |
| Crystal system | Monoclinic | Monoclinic | Monoclinic |
| Space group | P 2$_1$/c | P2$_1$/n | P2$_1$/n |
| a/Å | 9.1670(6) | 10.021(4) | 7.493(2) |
| b/Å | 24.8802(15) | 13.135(6) | 19.263(5) |
| c/Å | 15.4087(9) | 12.733(6) | 12.710(3) |
| β/° | 99.275(1) | 97.358(5) | 103.926(3) |
| U/Å$^3$ | 3468.4(4) | 1675.7(5) | 1780.6(8) |
| Z | 4 | 4 | 4 |
| Dc/Mg m$^{-3}$ | 2.226 | 2.220 | 2.186 |
| μ/mm$^{-1}$ | 9.540 | 9.867 | 9.291 |
| Crystal size/mm | 0.18 × 0.18 × 0.18 | 0.28 × 0.22 × 0.08 | 0.18 × 0.02 × 0.02 |
| Reflections collected | 37881 | 18332 | 17540 |
| R(int) | 0.0543 | 0.0275 | 0.0639 |
| Data/restraints/parameters | 7583/0/322 | 3937/6/168 | 3402/0/174 |
| Absorption correction | Semi-empirical | Semi-empirical | Semi-empirical |
| R1 [I > 2 (I)] | 0.0290 | 0.0227 | 0.0316 |
| wR2 (all data) | 0.0696 | 0.0485 | 0.0743 |
| Largest peak, hole/e Å$^{-3}$ | 1.199, −0.664 | 1.191, −0.804 | 0.733, −0.825 |

The X-ray crystal data for complexes 3-6 and 8 are presented in Tables 1 and 2, and the X-ray crystal data for complexes 9, 10, and 11 are provided in Table 3.

The presence of a single unpaired f electron in the Ce(III) species somewhat limits the characterization techniques available for paramagnetic species 2-6. Given the potentially labile nature of some of the solvating ligands of the Ce(III) adducts, it was of interest to synthesize representative examples of the corresponding diamagnetic La(III) adducts. Thus, crystals of LaBr$_3$(THF)$_4$ (complex 7) and LaBr$_3$(MeCN)$_5$·2MeCN (complex 8) were prepared by dissolution of bulk LaBr$_3$ in the respective hot solvents with subsequent cooling. The structure of 7 was confirmed by matching of the unit cell to the published structure while the identity of 8 was established on the basis of single-crystal X-ray diffraction (see FIG. 5). Addition of an internal standard (hexamethylbenzene) in $^1$H NMR experiments demonstrated that while 7 retained the THF solvate molecules, 8 indicated loss of lattice MeCN molecules resulting in a composition of the formula of LaBr$_3$(MeCN)$_{4.5}$. The elemental analysis (EA) data for 8 is in agreement with this result, indicating a composition of LaBr$_3$(MeCN)$_{4.7}$. In the case of the Ce(III) analog, the EA data indicates a significant loss of acetonitrile (i.e. MeCN) solvate molecules resulting in the formula CeBr$_3$(MeCN)$_{2.8}$. This is further evidenced by the degradation of crystals of 4 to powder, also accompanied by a notable loss of mass. It is apparent that the MeCN adducts 4 and 8 are thermally unstable and readily de-solvate over time at room temperature. This feature is also observed in 3, with EA results yielding a formula of CeBr$_3$(2-Me-THF)$_{1.9}$. As with the MeCN adducts, de-solvation is evidenced by the observation that clear, colorless blocks of 3 turn to chalk-like solids over the course of a few hours. It is of interest to note that the THF analogs of 2 and 7 both maintain their original crystalline structure over the course of weeks at ambient temperature. Thus, it is highly likely that the additional steric constraints imposed by the presence of the 2-Me groups in 3 accounts for the destabilization of the molecular adduct.

The addition of a suitable ionic liquid (e.g. 1-butyl-1-methylpyrrolidinium bis(trifluoromethylsulfonyl)imide) to bulk CeBr$_3$ resulted in a precursor paste that enhances CeBr$_3$ solubility in THF, 2-Me-THF and MeCN. Recrystallization from the respective solvents resulted in the formation of CeBr$_3$(THF)$_4$, CeBr$_3$(2-Me-THF)$_4$ and CeBr$_3$(MeCN)$_5$·MeCN. The THF adduct proved to be a suitable precursor for the synthesis of CeBr$_3$(py)$_4$ and CeBr$_3$(bipy)(py)$_3$. LaBr$_3$(THF)$_4$ and LaBr$_3$(MeCN)$_5$ were independently prepared and characterized as diamagnetic analogs of their paramagnetic CeBr$_3$ counterparts. All new compounds were characterized by single crystal X-ray diffraction experiments and elemental analysis. The use of an ionic liquid to significantly increase isolable yields of cerium halide solvates is expected to impact the fields of general organolanthanide chemistry as well as lanthanide containing materials chemistry.

The foregoing description of the invention, has been presented for purposes of illustration and description and is not intended to be exhaustive or limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A process for preparing a cerium halide solvate complex, comprising:

forming a paste of a cerium(III) halide compound and a suitable ionic liquid, the cerium halide being selected from the group consisting of cerium(III) fluoride, cerium(III) chloride, cerium(III) bromide, and cerium(III) iodide, dissolving at least a portion of the paste into a suitable organic solvent to form either a liquid phase or a solid phase and a liquid phase, separating any remaining solid phase from the liquid phase, and forming crystals of the cerium(III) halide solvate complex from the liquid phase.

2. The process of claim 1, wherein the step of forming crystals of the cerium(III) halide complex comprises allowing vapor from a suitable organic liquid to diffuse into the liquid phase.

3. The process of claim 1, wherein the step of forming crystals of cerium(III) halide complex from the liquid phase comprises cooling the liquid phase in order to induce the growth of crystals from the liquid phase.

4. The process of claim 1, wherein the organic solvent is selected from an ether, a carboxylic acid, an ester, an aldehyde, a thiol, a mercaptan, a thioether, a thioester, a nitrile, an amine, a phosphine, and combinations thereof.

5. The process of claim 1, wherein the organic solvent is selected from diethylether, diisopropylether, diphenylether, formic acid, acetic acid, stearic acid, butyl butyrate, benzyl acetate, ethyl formate, benzaldehyde, butyraldehyde, acetaldehyde, 2-methyl-tetrahydrofuran, methanethiol, butanethiol, tert-butyl mercaptan, dimethylsulfide, diethylsulfide, thioanisole, S-methyl thioacetate, S-tertbutyl thioacetate, S-ethyl thiopropionate, tetrahydrothiophene, 2,6-pyridinedicarhothioic acid, acetronitrile, benzonitrile, glutaronitrile, 2-methylpyridine, 3,5-dimethylpyridine, 4-methylpyridine, tert-butylamine, isopropylamine, triethylphosphine, trimethylphosphine, and combinations thereof.

6. The process of claim 1, wherein the ionic liquid is 1-butyl-1-methylpyrrolidinium bis(trifluoromethylsulfonyl) imide.

7. A process for preparing cerium(III) halide solvate complexes, comprising:
   combining a suitable ionic liquid with a first cerium(III) halide solvate and a suitable coordinating solvent to form a solid phase and a liquid phase,
   separating the solid phase from the liquid phase, and
   forming crystals of a second cerium(III) halide solvate from the liquid phase.

8. The process of claim 7, wherein the first cerium(III) halide solvate complex is $CeBr_3(tetrahydrofuran)_4$ and the coordinating solvent is a polyether.

9. The process of claim 7, wherein the ionic liquid is 1-butyl-1-methylpyrrolidinium bis(trifluoromethylsulfonyl) imide.

10. The process of claim 8 where the polyether is selected from dimethoxyethane, diglyme, and tetraglyme.

* * * * *